United States Patent
Selover et al.

(10) Patent No.: US 8,430,813 B2
(45) Date of Patent: Apr. 30, 2013

(54) ILLUMINATED SURGICAL ACCESS SYSTEM INCLUDING A SURGICAL ACCESS DEVICE AND INTEGRATED LIGHT EMITTER

(75) Inventors: Sean Selover, Westport, MA (US); Sara Dziedzic, Dorchester, MA (US); Steve Connolly, Sharon, MA (US); Anita Barnick, Berkley, MA (US); Erin Dupak, Fall River, MA (US)

(73) Assignee: DePuy Spine, Inc., Raynham, MA (US)

( * ) Notice: Subject to any disclaimer, the term of this patent is extended or adjusted under 35 U.S.C. 154(b) by 531 days.

(21) Appl. No.: 11/441,753

(22) Filed: May 26, 2006

(65) Prior Publication Data

US 2007/0276191 A1 Nov. 29, 2007

(51) Int. Cl.
*A61B 1/32* (2006.01)

(52) U.S. Cl.
USPC ............................... 600/245; 600/215

(58) Field of Classification Search ........... 600/201–245
See application file for complete search history.

(56) References Cited

U.S. PATENT DOCUMENTS

| | | | |
|---|---|---|---|
| 1,326,300 A | 12/1919 | Smit | |
| 2,235,979 A | 3/1941 | Brown | |
| 3,075,516 A | 1/1963 | Strauch | |
| 3,261,350 A | 7/1966 | Wallace | |
| 3,436,141 A | 4/1969 | Comte | |
| 3,590,232 A | 6/1971 | Sadowski | |
| 3,664,330 A | 5/1972 | Deutsch | |
| 4,173,392 A | 11/1979 | Ekinaka et al. | |
| 4,215,678 A | 8/1980 | Heine et al. | |
| 4,300,541 A | 11/1981 | Burgin | |
| 4,500,181 A | 2/1985 | Takahashi et al. | |
| 4,562,832 A | 1/1986 | Wilder et al. | |
| 4,597,030 A | 6/1986 | Brody et al. | |
| 4,802,460 A | 2/1989 | Ohkuwa et al. | |
| 4,805,984 A | 2/1989 | Cobb, Jr. | |
| 4,905,082 A | 2/1990 | Nishigaki et al. | |
| 4,907,132 A | 3/1990 | Parker | |
| 5,039,198 A | 8/1991 | VanBeek | |

(Continued)

FOREIGN PATENT DOCUMENTS

| DE | 3419324 C1 | 8/1985 |
|---|---|---|
| DE | 19732785 A1 | 2/1999 |

(Continued)

OTHER PUBLICATIONS

European Office Action for Application No. 07795421.2, dated Nov. 26, 2010.

(Continued)

*Primary Examiner* — Eduardo C Robert
*Assistant Examiner* — James Palmer
(74) *Attorney, Agent, or Firm* — Nelson Mullins Riley & Scarborough LLP

(57) ABSTRACT

A surgical access system for providing access to a surgical site in a patient includes a surgical access device defining a working channel for accessing a surgical site and an integrated light emitter for illuminating the surgical site. The light emitter is integrated in proximity to a distal end of the surgical access device. In some embodiments, the light emitter is offset from the distal end. In certain embodiments, the integrated light emitter includes a light transmission medium for transmitting light from a proximal end of the access device to the distal end.

6 Claims, 10 Drawing Sheets

U.S. PATENT DOCUMENTS

| | | | |
|---|---|---|---|
| 5,165,387 A | 11/1992 | Woodson | |
| 5,261,392 A | 11/1993 | Wu | |
| 5,334,150 A | 8/1994 | Kaali | |
| 5,353,786 A | 10/1994 | Wilk | |
| 5,354,302 A | 10/1994 | Ko | |
| 5,400,773 A | 3/1995 | Zhu et al. | |
| 5,441,041 A | 8/1995 | Sauer et al. | |
| 5,445,142 A | 8/1995 | Hassler, Jr. | |
| 5,448,990 A | 9/1995 | De Faria-Correa et al. | |
| 5,562,696 A | 10/1996 | Nobles et al. | |
| 5,584,796 A | 12/1996 | Cohen | |
| 5,588,949 A | 12/1996 | Taylor et al. | |
| 5,588,951 A | 12/1996 | Zhu et al. | |
| 5,591,192 A | 1/1997 | Privitera et al. | |
| 5,630,795 A | 5/1997 | Kuramoto et al. | |
| 5,759,150 A | 6/1998 | Konou et al. | |
| 5,785,648 A | 7/1998 | Min | |
| 5,817,005 A | 10/1998 | Cohen | |
| 5,891,013 A | 4/1999 | Thompson | |
| 5,957,832 A * | 9/1999 | Taylor et al. | 600/114 |
| 5,967,971 A | 10/1999 | Bolser | |
| 6,129,662 A | 10/2000 | Li et al. | |
| 6,139,493 A * | 10/2000 | Koros et al. | 600/215 |
| 6,176,824 B1 | 1/2001 | Davis | |
| 6,185,356 B1 | 2/2001 | Parker et al. | |
| 6,196,968 B1 | 3/2001 | Rydin et al. | |
| 6,210,325 B1 | 4/2001 | Bartie et al. | |
| 6,304,712 B1 | 10/2001 | Davis | |
| 6,427,034 B1 | 7/2002 | Meis et al. | |
| 6,504,985 B2 | 1/2003 | Parker et al. | |
| 6,551,346 B2 | 4/2003 | Crossley | |
| 2002/0080248 A1 | 6/2002 | Adair et al. | |
| 2003/0163030 A1 | 8/2003 | Arriaga | |
| 2004/0097794 A1 | 5/2004 | Bonutti et al. | |
| 2004/0141302 A1 | 7/2004 | Koch et al. | |
| 2004/0141336 A1 | 7/2004 | West et al. | |
| 2004/0143167 A1 * | 7/2004 | Branch et al. | 600/212 |
| 2004/0143169 A1 * | 7/2004 | Branch et al. | 600/245 |
| 2005/0070765 A1 * | 3/2005 | Abdelgany et al. | 600/214 |
| 2005/0203341 A1 | 9/2005 | Welker et al. | |
| 2005/0256525 A1 | 11/2005 | Culbert et al. | |
| 2005/0277811 A1 | 12/2005 | Richards et al. | |
| 2006/0069313 A1 | 3/2006 | Couvillon et al. | |
| 2006/0069314 A1 | 3/2006 | Farr | |
| 2006/0224045 A1 * | 10/2006 | Whipple et al. | 600/245 |

FOREIGN PATENT DOCUMENTS

| | | |
|---|---|---|
| EP | 0566359 A2 | 10/1993 |
| GB | 2133694 A | 8/2004 |
| WO | 2005/016131 A2 | 2/2005 |

OTHER PUBLICATIONS

Japanese Office Action for Application No. 2009-512181, 10 pages, dated Mar. 6, 2012.

International Search Report for Application No. PCT/US2007/12614, dated May 8, 2008.

European Office Action for Application No. 07795421.2, 5 pages, dated Oct. 1, 2012.

* cited by examiner

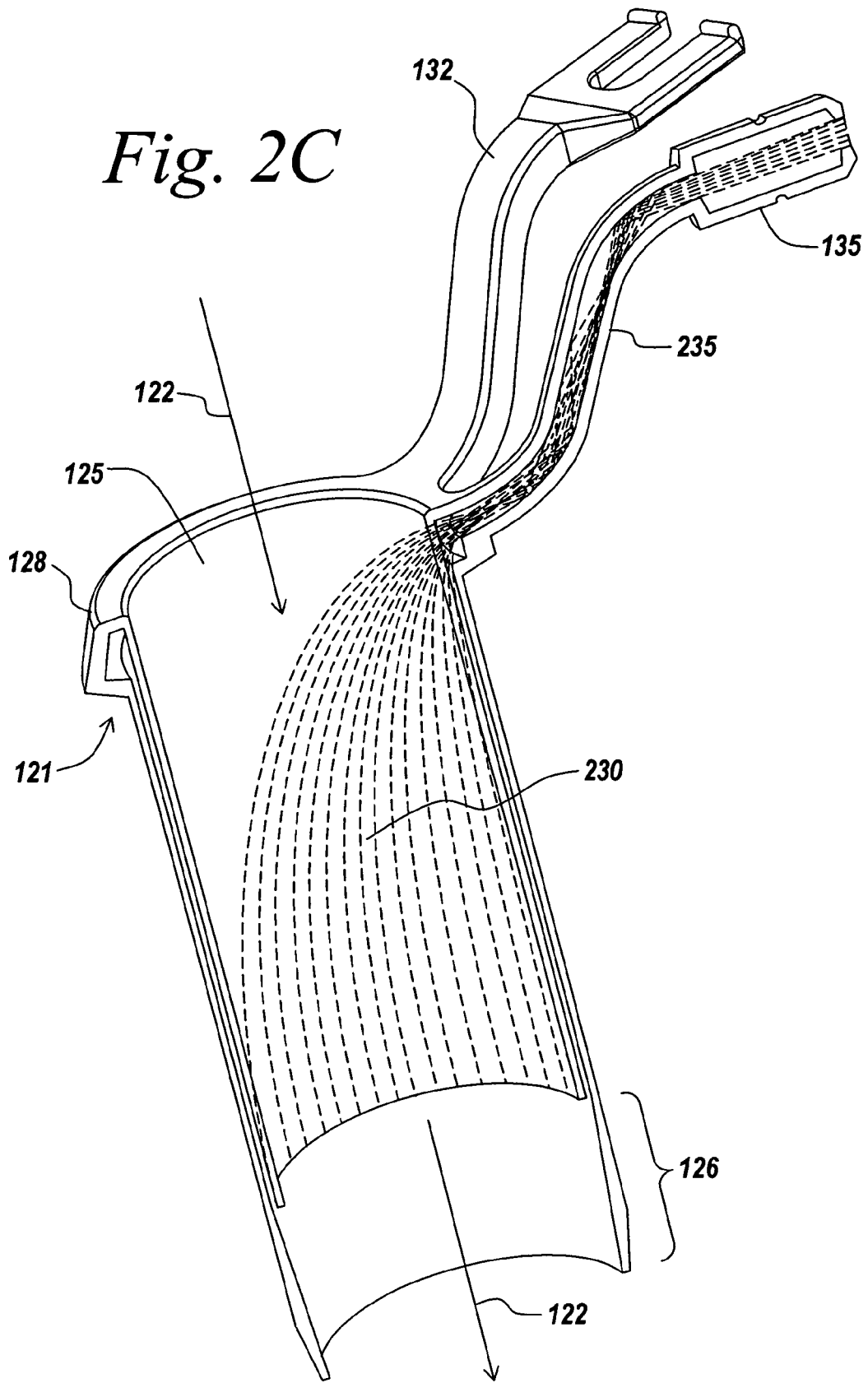

ILLUMINATED SURGICAL ACCESS SYSTEM INCLUDING A SURGICAL ACCESS DEVICE AND INTEGRATED LIGHT EMITTER

FIELD OF THE INVENTION

The present invention relates to devices used in surgery. More particularly, the present invention relates to instrumentation and a method for the providing of access and illumination for surgical sites, implements and implants.

BACKGROUND OF THE INVENTION

In minimally invasive surgical procedures, illumination of a working space may be required to facilitate use of surgical instruments. For example, in spinal surgery, access ports, comprising generally tubular, open-ended structures, are often used to provide access to a surgical site. The access ports may require illumination at the distal end thereof to facilitate the surgical procedure.

Achieving proper illumination of a surgical site during minimally invasive surgery can be difficult. In the current state of the art, external light sources are used to provide illumination to access ports. However, external light sources are unwieldy, and the link used to transmit the generated light to the access port can be cumbersome and block access by a surgeon to the port. For example, a surgeon may wear a head-mounted light in order to illuminate the working area at the base of an access port. Head-mounted light sources may require the surgeon to constantly direct the light with his or her head at an optimal angle, into the access port in order to view the working area. Also the light source is distant from the surgical site, increasing the likelihood of creating shadows and potentially obstructing the ability of the light to reach the working area when using surgical instruments inside the port. In addition, fiber optic cables, attached to the light, can encumber the surgeon and tether him or her to a light source.

Another option currently used by surgeons involves lights mounted on an overhead microscope. Though offering an un-tethered light source that can be positioned accurately above the port, one main limitation still exists in that the light source is still distant from the surgical site. Again this increases the likelihood of creating shadows and potentially obstructing the ability of the light to reach the working area.

Other alternatives for lighting a surgical site attach light sources into the interior of an access port to illuminate the work space. However, the use of a light source within the access port can reduce the available working area in the port and may hinder the use of instruments that enter and exit the port during surgery.

SUMMARY OF THE INVENTION

The present invention provides an illuminated surgical access system including a light emitter coupled to a surgical access device. The surgical access device defines a path or port to a surgical site and the light emitter emits and directs light into the path to illuminate a surgical site accessed by the surgical access device. The light emitter is integrated into the distal end of the access device to provide illumination of the working site and provides circumferential light about an interior path via the side walls of the surgical access device. Preferably the light emitter is offset from the very distal tip of the access device to prevent tissue or other biological matter from blocking the transmission of light. The integrated light emitter may be comprised of a light transmission medium integrated into the sidewall which transfers light provided at the proximal end of the port to the surgical site. The integrated light emitter does not reduce the working area of the access device or hinder the surgeon, while providing superior illumination of a surgical site.

According to a first aspect of the invention, an illuminated surgical access system is provided for creating access to a patient's bony anatomy during surgery. The illuminated surgical access system includes a surgical access device including at least one sidewall and defines an interior path therethrough forming a port for accessing the patient, and a light emitter integrated into the sidewall in proximity to a distal end of the access device to illuminate a surgical site accessed by the surgical access device.

According to another aspect of the invention, a method of accessing a surgical site in a patient is provided. The method comprises the steps of creating an incision in the patient, inserting a surgical access device into the incision in the patient. The surgical access device comprises at least one sidewall and defines an interior path therethrough forming a port for accessing the patient; and a light emitter integrated into the sidewall in proximity to a distal end of the access device to illuminate a surgical site accessed by the surgical access device. The surgical site may then be illuminated using the surgical access device.

According to another aspect of the invention, an illuminated surgical access system is provided for creating access to a surgical site of a patient during surgery. The illuminated surgical access system including a retractor comprising one or more blades defining an interior path therethrough forming a path for accessing the surgical site, and an integrated light emitter in proximity to a distal end of the one or more blades of the retractor to illuminate a surgical site accessed by the retractor.

According to another aspect of the invention, a method of accessing a surgical site in a patient is provided. The method includes the steps of creating an incision in the patient and inserting a retractor into the incision in the patient. The surgical access device includes one or more blades defining an interior path therethrough forming a port for accessing the patient, and an integrated light emitter in proximity to a distal end of the one or more blades of the retractor to illuminate a surgical site accessed by the retractor. The surgical site may then be illuminated using the retractor.

BRIEF DESCRIPTION OF THE FIGURES

These and other features and advantages of the present invention will be more fully understood by reference to the following detailed description in conjunction with the attached drawings in which like reference numerals refer to like elements through the different views. The drawings illustrate principles of the invention and, although not to scale, show relative dimensions.

FIGS. 2A-2C illustrate an illuminated surgical access system including a light emitter comprising a light transmission medium according to one embodiment of the invention.

DETAILED DESCRIPTION OF THE INVENTION

The present invention provides an improved surgical access system for accessing a surgical site. The surgical access system includes an integrated light emitter for illuminating the surgical site. The present invention will be described below relative to certain illustrative embodiments. Those skilled in the art will appreciate that the present invention may be implemented in a number of different applications and embodiments and is not specifically limited in its application to the particular embodiments depicted herein.

The illuminated surgical access system of the illustrative embodiment of the invention may be used in spinal surgery, for example, during a discectomy or microdiscectomy procedure to remove damaged disc material from the spine. One skilled in the art will recognize that the invention can be used with other surgical instruments in other surgical procedures that require illumination. Examples of surgical procedures suitable for employing the illuminated surgical access system of the present invention include, but are not limited to, insertion of interbody fusion devices, bone anchors, fixation devices, including rods, plates and cables, artificial disks, hip stems, artificial ligaments, trochars for gastro-intestinal work, or any procedure requiring access to a patient and visualization. The surgical access system may be part of any suitable implant instrument used to provide access to a particular area of a patient's body where visualization is also needed. The surgical access system can be used to position any suitable implant, instrument and/or other device in any suitable procedure where guidance of the implant, instrument and/or device is used. Alternatively, or in addition to providing guidance, the surgical access system may be used to dilate a surgical incision using a set of progressively larger cannulas or an expanding cannula to provide access to a surgical site.

An illustrative embodiment of the present invention provides lighted, minimally invasive access to a surgical site via a low profile port that used integrated light transmission and emission technology. The invention facilitates access to a surgical site without decreasing a working space in the port or requiring extra equipment to be worn by the surgeon.

Figure 1A:
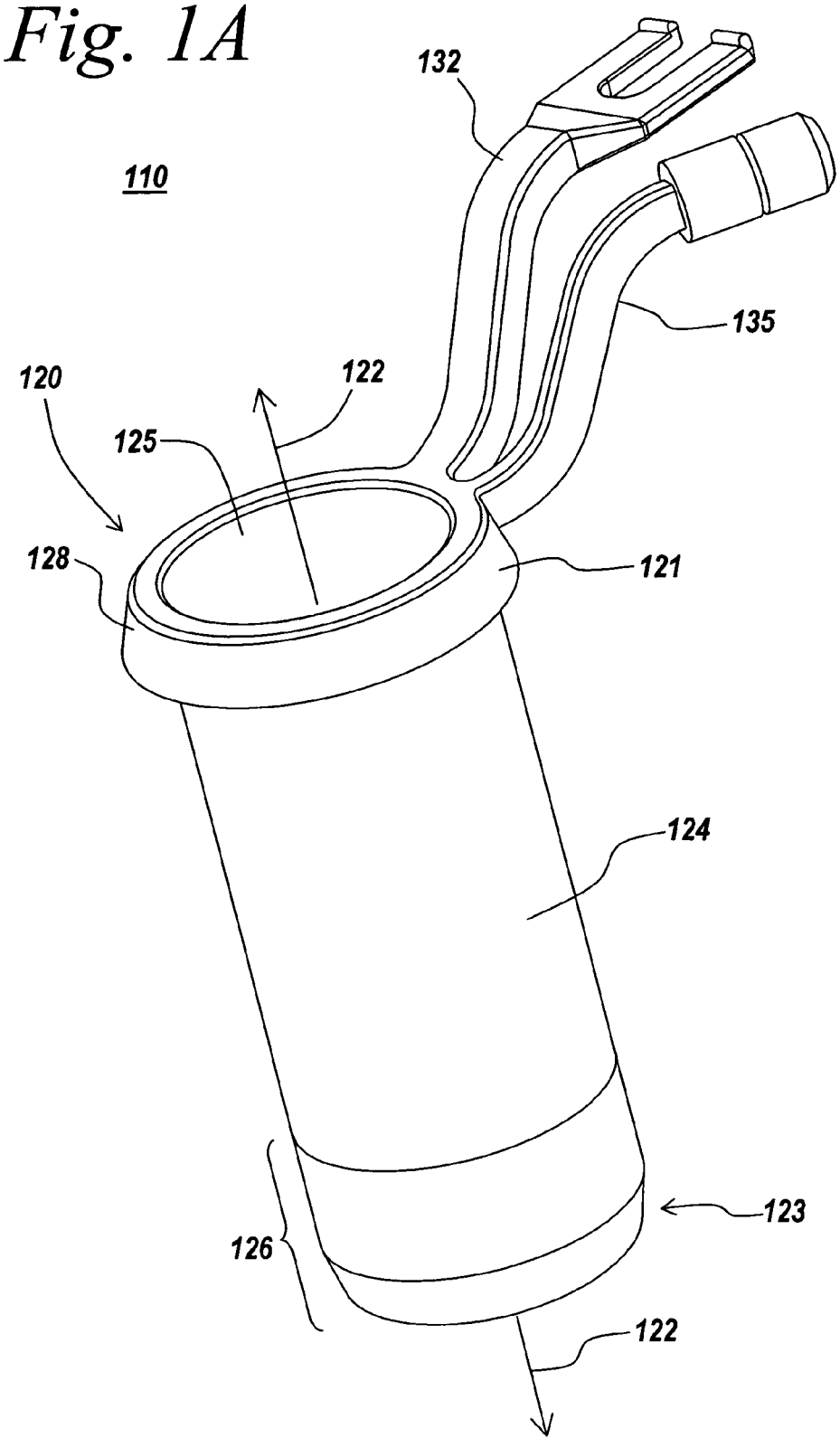
FIG. 1A-1B illustrate an illuminated surgical access system including a light emitter coupled to a proximal end of an access device according to an embodiment of the invention.
Figure 1B:
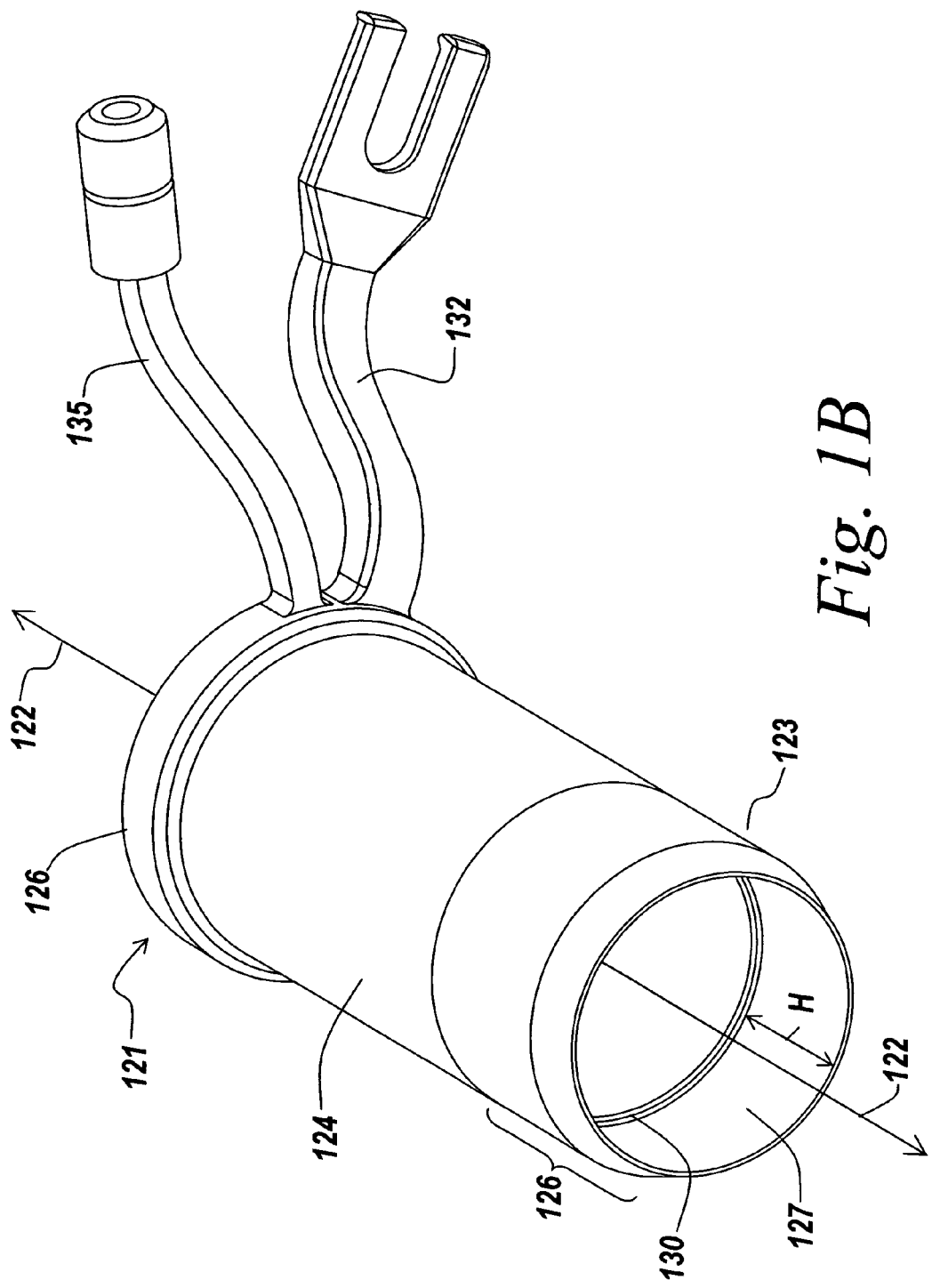

FIGS. 1A and 1B illustrate different perspective views of an illuminated surgical access system of an illustrative embodiment of the invention for providing both access and illumination of a surgical site during performance of a surgical procedure. The illustrative illuminated surgical access system 110 includes a port, illustrated as an access device 120 comprising a substantially hollow tubular body, for accessing a surgical site, and a light emitter 130 integrated into the sidewall 124 in proximity to a distal end 123 of the surgical access device 120 for illuminating an a surgical site.

The illustrative access device 120 may be a standard access port, in the shape of a cannula comprising a hollow tubular body suitable for insertion in and/or placement adjacent to a patient's body. The illustrative access device 120 has at least one hollow channel or lumen defining an interior path 122 extending from an open proximal end 121 of the access device to an open distal end 123 of the access device. The path 122 may form a working channel or at least a portion of a working channel for accessing a surgical site adjacent to or in the vicinity of the distal end 123 of the tubular body. In the illustrative embodiment, the body of the access device 120 includes open proximal end 121 that forms a proximal port 125 of the interior path 122, and the open distal end 123 forms a distal port 127 of the interior path 122 for allowing access to the surgical site. One skilled in the art will recognize that the access device 120 may have any suitable configuration and size for providing access to an area of a body. The illustrative access device may be used for retaining soft tissue away from a surgical site and/or guiding a surgical instrument, device and/or implant, though one skilled in the art will recognize that the access device may comprise any suitable device defining a path or channel requiring illumination.

As shown, the tubular body of the illustrative access device 110 is formed by a cylindrical sidewall 124 preferably having smooth inner and outer surfaces, though one skilled in the art will recognize that the tubular body can have any size, shape, configuration and number of sidewalls. The access device can be any suitable device defining a port for providing access to a surgical site. The access device can have any suitable cross-section and is not limited to the cylindrical cross-section shown in the illustrative embodiments. The access device can be open or closed to define an open or closed path therethrough.

The surgical access device 120 can be formed of any suitable surgical material, such as, but not limited to, plastic, surgical stainless steel and other materials known in the art. An example of a suitable material is opaque PEEK or other opaque plastics, though other materials may also be used. The surgical access device may also be made of a combination of suitable materials such as opaque PEEK and Surgical Stainless Steel.

The tubular body of the illustrative access device can be rigid, semi-rigid or flexible, and can have any suitable size, shape and configuration suitable for defining a working channel and/or access to a surgical site. In the illustrative embodiment, the tubular body is straight to define a straight channel therethrough, though one skilled in the art will recognize that the tubular body may define a shaped trajectory therethrough. The tubular body is not limited to a tubular structure having closed sidewalls and can be any component that defines a path, including an open channel or a solid member. In some embodiments, the access device may also means 132 for attaching the access device 120 to an arm for securing the position of the access device 120.

The path through the access device may also or alternatively form a working channel configured to receive selected surgical instruments, such as awls, bone taps, obturators, drills, guide wires, and/or implants, such as screws, fusion devices, artificial disks and hip stems, along the longitudinal axis thereof.

In one embodiment, the illuminated access device 110 may be configured to guide instruments along the working channel. In such an embodiment, the inner diameter of the tubular body may be slightly larger than the outer diameter of the instrument guided by the tubular body, so that the instrument can be inserted through the tubular body while the sidewalls of the tubular body maintain the instrument at a predetermined angle relative to the patient. Alternatively, an instrument to be guided by the tubular body can be configured to slide over the tubular body, with the tubular body maintaining the orientation of the instrument as the instrument slides relative to the tubular body. In this embodiment, the tubular body can have an outer diameter that is slightly less than an inner diameter of an instrument. However, the access device 110 need not form a trajectory or guide for instruments and can be any device suitable for providing access to a surgical site.

In certain embodiments, the proximal end 121 forming the proximal port 125 may be configured to minimize reflection of overhead light so as to reduce glare for the surgeon using the access device 110. In one example, as seen in FIG. 1A, the lip 128 of the proximal port 125 is chamfered to prevent overhead light from reflecting back into the surgeons eyes. In another embodiment, the surface of the proximal end may be treated to make the surface non-reflective. For example, the surface may be etched, coated with a non-reflective coating, or otherwise surfaced to reduce reflection. It will be understood that these are but some of the possible configurations and other implementation or combinations of the above are possible.

The light emitter 130 is integrated into the side wall 124 at the distal end 123 of the access device 120. Preferably, the light emitter 130 emits circumferential light into the interior of the access device 120 directly inside and about the inner circumference of the distal end 123, or about at least a substantial portion of the inner circumference. For example, for an access device that has an open side, the light emitter 130 may distribute light about perimeter of the side wall and may or may not distribute light where the side wall of the access device is open. Similarly, for an arc-shaped access device, the inner circumference refers to the inner edge of the arc and is not required to be a full circle or loop. The light emitted into the tube interior is directed through path 122, out distal port 127 and into a working space adjacent to the distal port 127.

The integrated light emitter 130 in the surgical access system of the illustrative embodiment of the invention can comprise any suitable means for producing light that may be directly integrated with the tubular body of an access device. The integrated light emitter easily integrates illumination into a surgical access device, without requiring cumbersome cables, while allowing direction of light to an ideal location. The integrated light emitter does not compromise or reduce the working area, as it is incorporates into the sidewall of the surgical access device and keeps the interior of the surgical access device clear. The integrated light source provides superior illumination by providing even, circumferential light distributed about the periphery of a surgical access device, preferably in the interior of the surgical access device.

Preferably the light emitter 130 is offset or recessed from the distal tip 126 of the access device 120. The distal end 123 of the access device 120 is inserted into a patient and the side wall 124 is used to hold tissue away from the surgical site providing access for a surgeon. Since the distal end 123 is placed as the location for which access is desired, the distal tip 126 of the access device 120 may be in direct contact with tissue which may cover or other wise block illumination of a light emitter 130 located on the distal tip 126. Offsetting the light emitter 130 reduces the likelihood of tissue or other biological matter of blocking the transmission of light or otherwise interfering with the illumination. The offset H is between approximately 1 and approximately 30, more preferably between approximately 10 and approximately 20 mm, and in one exemplary embodiment is approximately 15 mm. Other possible configurations will be apparent to one skilled in the art give the benefit of this disclosure.

In some embodiments the light emitter 130 may be configured to focus light at a particular point in the distal port 127. In other embodiments, the light emitter 130 may be configured to provide defuse ambient light across the surgical site. Other possible implementations and configurations will be apparent to one skilled in the art given the benefit of this disclosure.

Figure 2A:
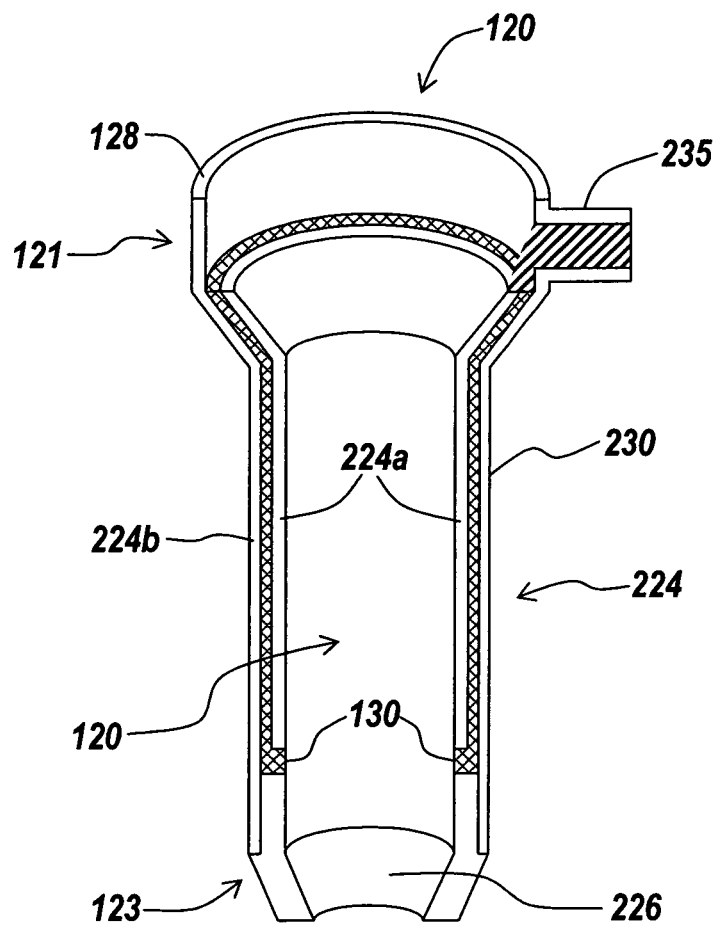

In certain embodiments, the light emitter 130 comprises a light transmission medium 230 for transmitting light, received for example via a coupler 135, from the proximal end 121 of the access device 120 to the distal end 123 of the device. In one example, as shown in FIG. 2A, the light transmission medium 230 is fiber optic cabling. In this embodiment, the light transmission medium 230, in this case fiber optics, is disposed between and inner surface 224a and an outer surface 224b of the side wall 124 of the access device 120.

Figure 2B:
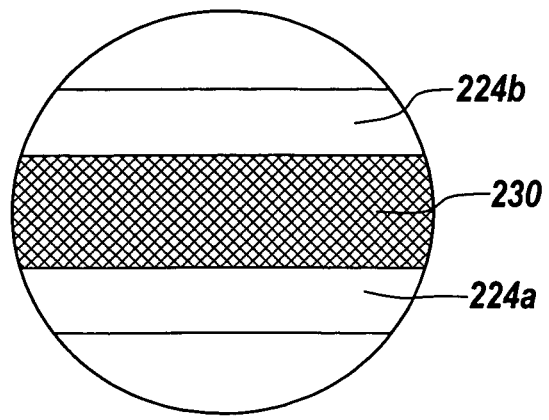

Disposing the transmission medium 230 between an inner 224a and outer 224b surface of the sidewall provides protection for the transmission medium. A close-up of a cross-section of the access device depicting this can be seen in FIG. 2B. In certain embodiments the inner 224a and outer 224b surfaces may be made of different materials. For example, the outer surface 224b may be made of metal for durability while the inner layer 224a may be made of a non-conductive or non-reactive material such as a polymer. Likewise the distal end 226 may be made of a different material. For example, since the distal end 226 is in contact with the surgical site it may be beneficial to have the distal end 226 made of a softer or non-reactive material. Examples of suitable materials have been set forth above and other embodiments will be apparent to one skilled in the art given the benefit of this disclosure. In one exemplary embodiment, the distal end is constructed from PEEK and or other suitable polymers. The inner and outer surfaces 224a and 224b are constructed of surgical stainless steel or other suitable metals. The distal end 226 of the exemplary embodiment can be manufactured separate from the inner and outer surfaces 224a, 224b and can be connected to the inner and outer surfaces 224a, 224b by for example, a snap fit, threads, bonding, or other conventional connection mechanisms.

FIG. 2C provides a view of the access device 120 showing the distribution of the transmission medium 230, in this case fiber optics, around the periphery of the sidewall 124 so as to provide a circumferential light source 130 offset from the distal end 226. Here, the transmission medium 230 is terminated within the inner path 122 so as provide a light emitter 130 at the distal end 123 of the access device. Depending on how the transmission medium 230, in this case the fiber optics, is terminated, the light emitter 130 may provide focused or defused. It should be understood that other transmission mediums and configurations are possible and will be apparent to one skilled in the art given the benefit of this disclosure.

The light transmission is configured at the proximal end 121 of the access device for receiving a light transferring cable (not shown) coupled to a light source (not shown). In the example of FIGS. 2A and 2C the fiber optics are bundled together 235 in a coupler 135 for connecting to a light source via a light transferring cable. In such embodiments, an external light source may be used to provide light to the coupler 135 of the access device which is transmitted from the proximal end 121 to the distal end 123 via the transmission medium. The light source may be any suitable device for producing light, including, but not limited to, halogen light boxes, incandescent light boxes and other light sources readily available in most hospital settings, such as those available from Welch Allyn Medical Products of Skaneateles Falls, N.Y. The light source may have any suitable power level. In an illustrative embodiment, the light source is a 300 Watt Halogen Light Box. Any other suitable light source capable of producing light that is transmitted to the light emitter 130 via the light transferring cable, which may be fiber optic cables or any other suitable light transmitter, may also be used.

In the above examples, the light emitter 130 emits white light. It will be understood that in some implementations it may be beneficial to provide other types of light. For example, in one embodiment, the light emitter 130 may emit infrared (IR) light or ultraviolet (UV) light which may used to illuminate IR or UV markers or cure IR or UV reactive epoxies or adhesives. Other possible implementations or applications will be apparent to one skilled in the art given the benefit of this disclosure.

Figure 3:
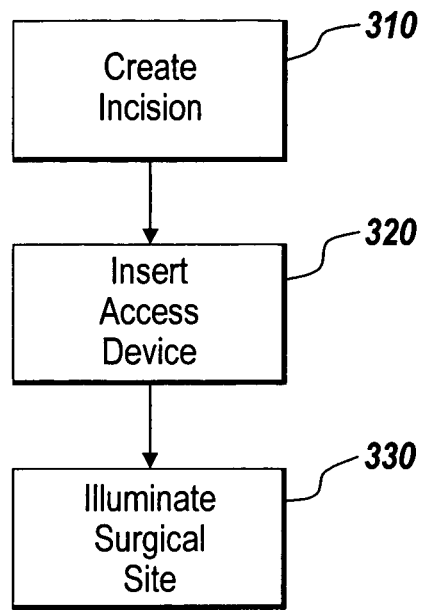
FIG. 3 is flow diagram of one exemplary embodiment of a method or preparing a surgical site using the illuminated surgical access system of the present invention.

FIG. 3 depicts a flow chart 300 of an exemplary embodiment of a method of preparing a surgical site using the present invention. The first step involves creating an incision in the patient (step 310). Once and incision has been created an access device of the present invention may be inserted into the incision (step 320). The surgical site may then be illuminated using the access device (step 330). These steps are discussed in more detail below.

In some embodiments, the method includes making a first incision in the epidermis of the patient and then expanding the incision into a portion of the subdermal tissue to create a pathway in any conventional manner. For example, the incision can be expanded by dilation to the desired shape, and orientation by using a plurality of dilators. Once the incision has been expanded to the desire size, shape, and orientation the retractor may be inserted.

Figure 4:
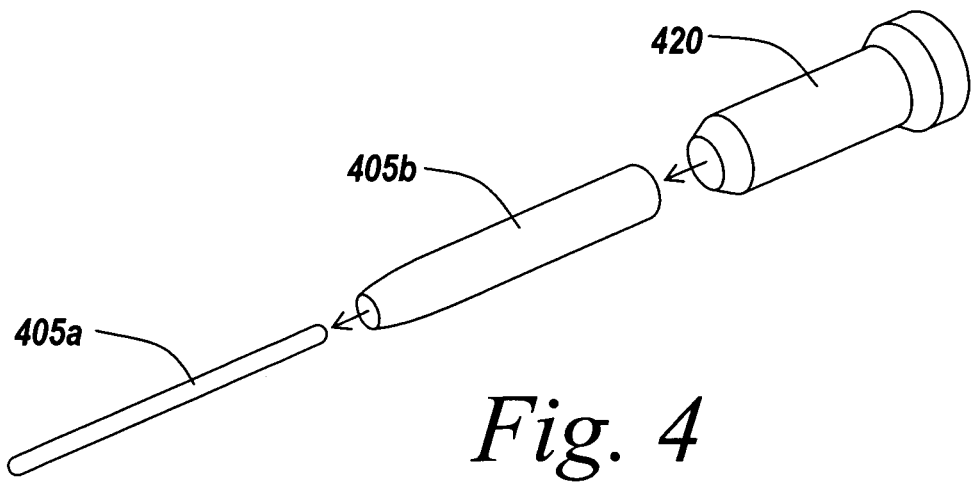
FIG. 4 illustrates one technique for inserting an access device according to the method of FIG. 3.

In the embodiment of FIG. 4, serial dilation is used to prepare the incision for the insertion of the access device 120. As such a series of dilators 405a, 405b may be inserted into the patient through the incision (not shown). The access device 120 may then be inserted into the patient over the dilators 405a, 405b. The dilatators 405a, 405b passing though the access device 120 serve as a guide for the insertion of the access device 120.

It should be understood that the above embodiments are exemplary. Other possible insertion techniques with or without insertion instruments as well as different insertion instruments are possible. Other implementations and configurations will be apparent to one skilled in the art given the benefit of this disclosure.

Once the access device 120 has been inserted the surgical site may then be illuminated. In some embodiments this may involve connecting the access device to an external light source 152 via a light transferring cable 150 and transmitting light from the external source 152 from the light emitter 130 incorporated into the sidewall as depicted in FIGS. 1 and 2.

Figure 5A:
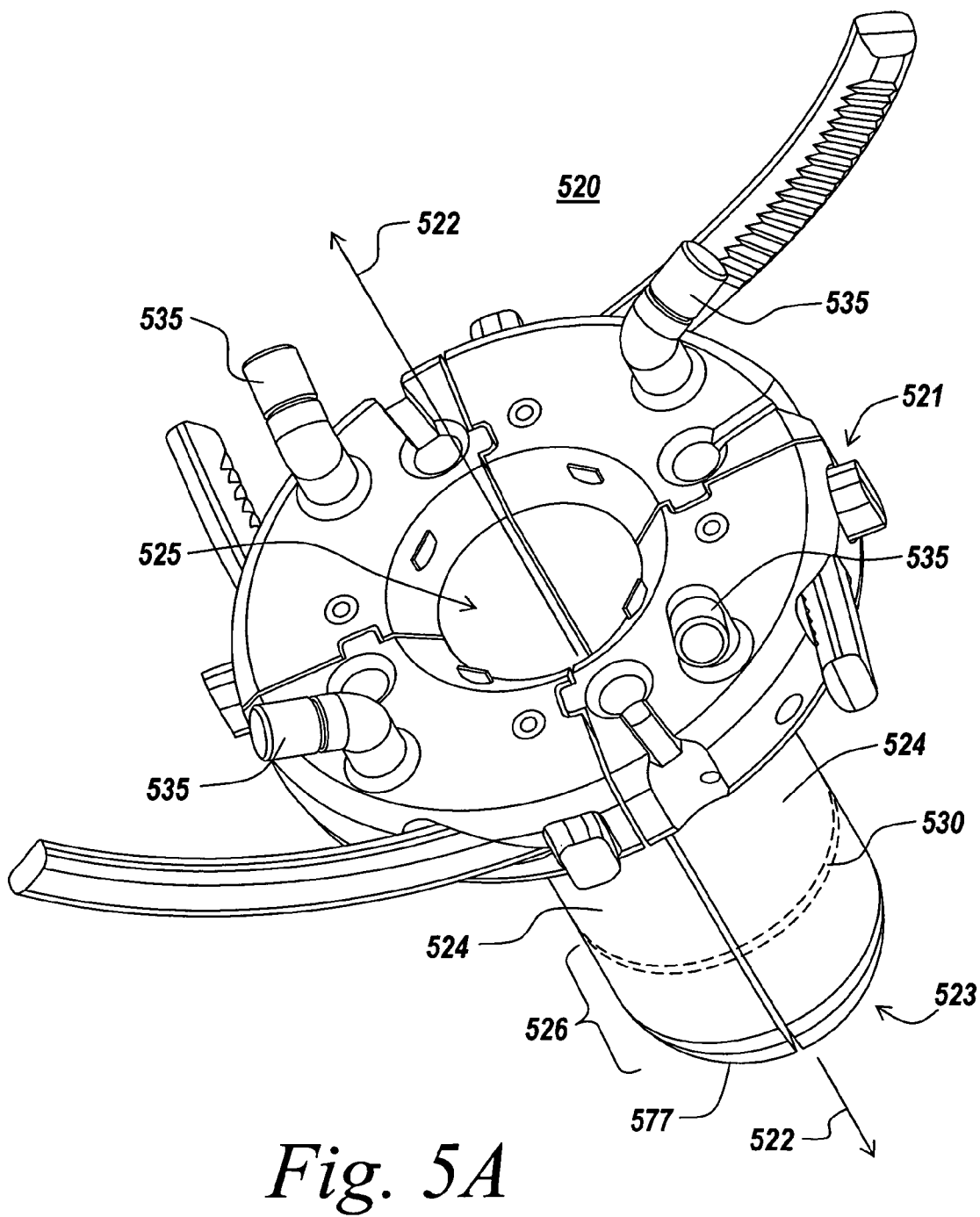
FIGS. 5A-5B illustrate an embodiment of an access device for an illuminated surgical access system wherein the access device is a retractor having one or more blades incorporating a light emitter.

In another example, the access device 510 may be a retractor 520 as shown in FIG. 5A. Here the retractor 520 comprises one or more adjustable blades 520 defining an interior path 522 therethrough forming a port for accessing the surgical site; and a light emitter 530 integrated into a distal end of the one or more adjustable blades 520 of the retractor to illuminate a surgical site accessed by the retractor.

The retractor 520 of FIG. 5A has an interior path 522 extending from an open proximal end 521 of the retractor 520 to an open distal end 523 of the retractor 520. The path 522 may form a working channel or at least a portion of a working channel for accessing a surgical site adjacent to or in the vicinity of the distal end 523 of the tubular body. In the illustrative embodiment, the body of the retractor 520 includes open proximal end 521 that forms a proximal port 525 of the interior path 522, and the open distal end 523 forms a distal port 527 of the interior path 522 for allowing access to the surgical site. One skilled in the art will recognize that the retractor 520 may have any suitable configuration and size for providing access to an area of a body.

The light emitter 530 is integrated into the blade 524 at the distal end 523 of the retractor 520. Preferably, the light emitter 530 emits light into the interior of the retractor 520 directly inside and about the inner circumference of the distal end 523, or about at least a substantial portion of the inner circumference. The light emitted into the interior is directed through path 522, out distal port 527 and into a working space adjacent to the distal port 527.

Preferably the light emitter 530 is offset or recessed from the distal tip 526 of the retractor 520. The distal end 523 of the retractor 520 is inserted into a patient and the blades 524 are used to hold tissue away from the surgical site providing access for a surgeon. Since the distal end 523 is placed as the location for which access is desired, the distal tip 526 of the access device 520 may be in direct contact with tissue which may cover or other wise block illumination of a light emitter 530 located on the distal tip 526. Offsetting the light emitter 530 reduces the likelihood of tissue or other biological matter of blocking the transmission of light or otherwise interfering with the illumination. The offset is between approximately 1 and approximately 30 mm, more preferably between approximately 10 and approximately 20 mm, and in one exemplary embodiment is approximately 15 mm. Other possible configurations will be apparent to one skilled in the art give the benefit of this disclosure.

Figure 5B:
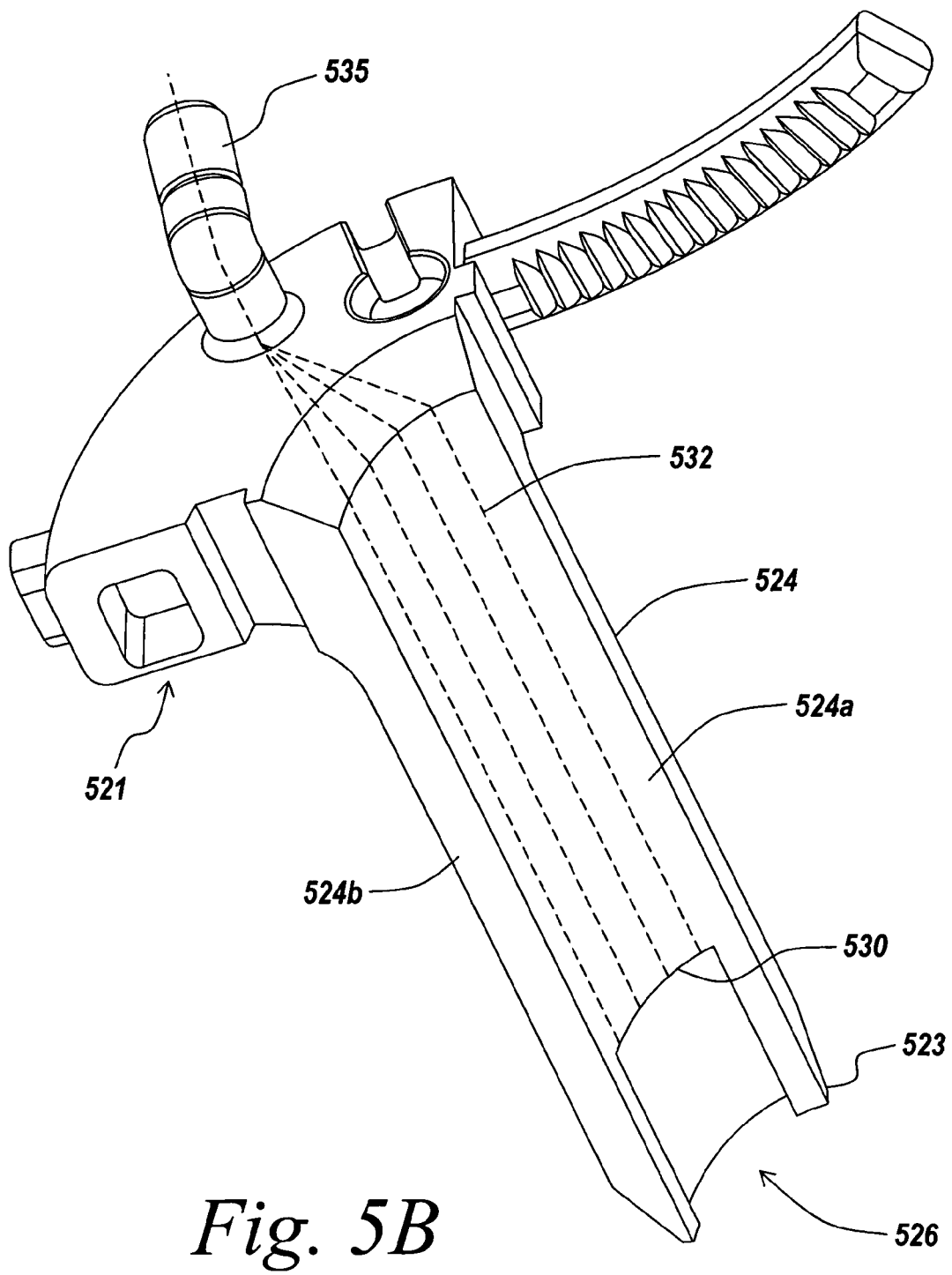

FIG. 5B depict one embodiment of a blade 524 of the retractor 520. In this example the blade 524 comprises an inner surface 524a and an outer surface 524b having a transmission medium 532, such as fiber optic cabling, providing a light transmission path. The transmission medium 532 further comprises connection 535 at the proximal end 521 for connecting the blade to an external light source such as shown in FIG. 1. The light transition medium 532 terminates at the distal end 523 in a light emitter 530. In this embodiment the light emitter 530 can be seen to be offset from the distal tip 526 of the blade 524.

Figure 6A:
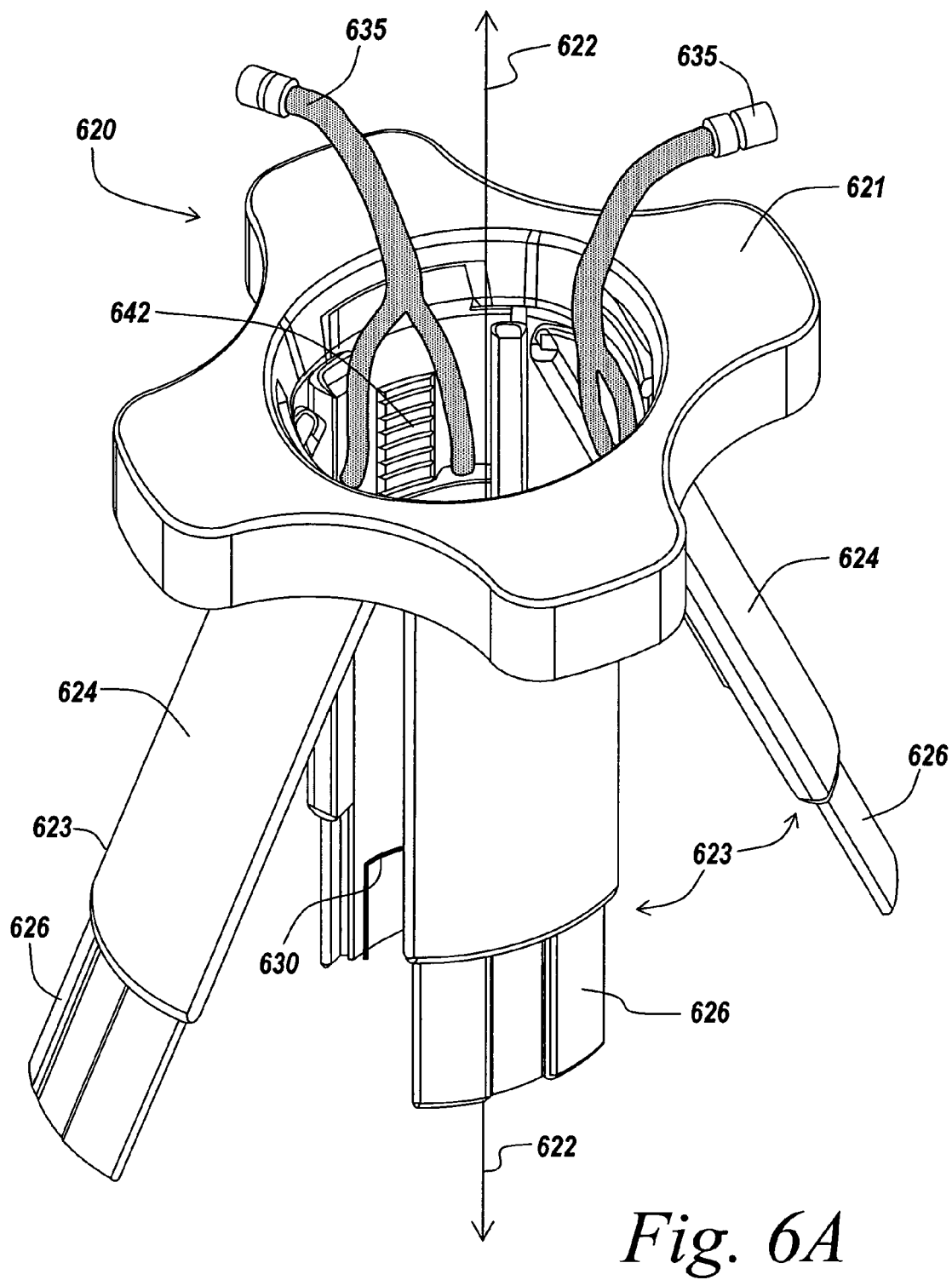
FIGS. 6A-6B illustrate another embodiment of an access device for an illuminated surgical access system wherein the access device is a retractor having one or more telescoping and rotatable blades incorporating a light emitter.

FIG. 6A depicts another embodiment of a retractor 620 wherein the adjustable blades 624 are telescoping and can rotate about an access. As with the retractor 520 of FIG. 5A, the retractor 620 of FIG. 6A has an interior path 622 extending from an open proximal end 621 of the retractor 620 to an open distal end 623 of the retractor 620. The path 622 may form a working channel or at least a portion of a working channel for accessing a surgical site adjacent to or in the vicinity of the distal end 623 of the tubular body. In the illustrative embodiment, the adjustable blades 624 of the retractor have been rotated outward, or "toed-in", as the adjustable blades 624 might be deployed in a patient to create a larger work area. In addition to being able to rotate, the adjustable blades in the present example are telescoping such that the distal end 626 of the adjustable blades 624 may be extended or retracted allowing for adjustable blade depth. One skilled in the art will recognize that the retractor 620 may have any suitable configuration and size for providing access to an area of a body.

The light emitter 630 is integrated into the blade 624 at the distal end 623 of the retractor 620. Preferably, the light emitter 630 emits light into the interior of the retractor 620 directly inside and about the inner circumference of the distal end 623, or about at least a substantial portion of the inner circumference into a working space defined by the retractor blades 624.

Preferably the light emitter 630 is offset or recessed from the distal tip 626 of a retractor blade 624. The distal end 623 of the retractor 620 is inserted into a patient and the blades 624 are used to hold tissue away from the surgical site providing access for a surgeon. Since the distal end 623 is placed as the location for which access is desired, the distal tip 626 of the access device 620 may be in direct contact with tissue which may cover or other wise block illumination of a light emitter 630 located on the distal tip 626. Offsetting the light emitter 630 reduces the likelihood of tissue or other biological matter of blocking the transmission of light or otherwise interfering with the illumination. The offset is between approximately 1 and approximately 30 mm, more preferably between approximately 10 and approximately 20 mm, and in one exemplary embodiment is approximately 15 mm. Other possible configurations will be apparent to one skilled in the art give the benefit of this disclosure.

Figure 6B:
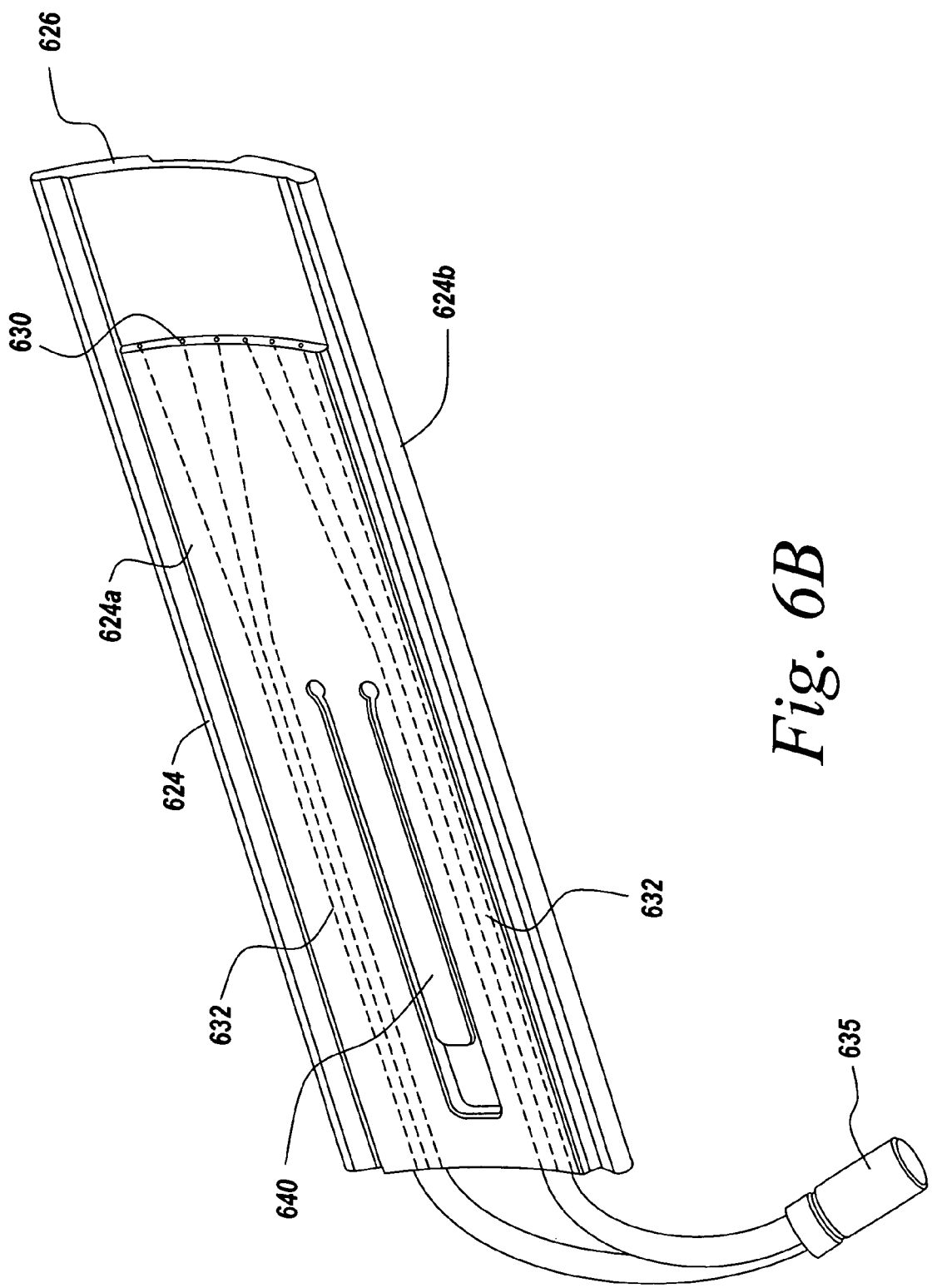

FIG. 6B depict one embodiment of a telescoping blade 624 of the retractor 620. In this example the blade 624 comprises an inner surface 624a and an outer surface 624b having a transmission medium 632, such as fiber optic cabling, providing a light transmission path. The transmission medium 632 further comprises a connection such as coupler 635 at the proximal end 621 for connecting the blade 624 to an external light source. The light transition medium 632 terminates at the distal end 623 in a light emitter 630. In this embodiment the light emitter 630 can be seen to be offset from the distal tip 626 of the blade 624. The exemplary blade 624 of FIG. 6B further includes configurations 640 for engaging surface configuration 642 on the retractor assembly 620 allowing the blade 624 to adjustably telescope when attached to the retractor assembly 620.

In the example, the transmission medium 630 is terminated so as provide a light emitter 130 at the distal end 123 of the access device. Depending on how the transmission medium 230, in this case the fiber optics, is terminated, the light emitter 130 may provide focused or defused light. It should be understood that other transmission mediums and configurations are possible and will be apparent to one skilled in the art given the benefit of this disclosure.

It should be understood that the retractors depicted in FIGS. 5A, 5B, 6A, and 6B are but some examples of any number of possible configurations for a retractor. Other possible configurations incorporating integrated light emitters will be apparent to one skilled in the art, given the benefit of this disclosure.

Figure 7:
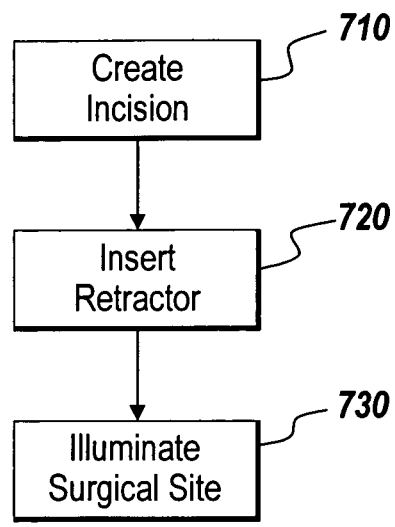
FIG. 7 is flow diagram of one exemplary embodiment of a method or preparing a surgical site using the illuminated surgical access system of the present invention.

FIG. 7 depicts a flow chart 700 of an exemplary embodiment of a method of preparing a surgical site using the present invention. The method involves the steps of creating and incision in the patient 710, inserting a retractor of the present invention into the incision 720, and illuminating the surgical site with the retractor 730.

The techniques for incision and serial dilation discussed above in regard to using and access device apply equally as well to the use of a retractor. The advantage of retractor is that after insertion, the retractor can be used to further dilate the incision and retract the tissue providing greater access to the surgical site.

The present invention has been described relative to an illustrative embodiment. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

The invention claimed is:

1. An illuminated surgical access system for providing access to a surgical site of a patient during surgery, comprising:
   a retractor comprising one or more adjustable blades in which depth of the blade is adjustable, the adjustable blade comprising an opaque inner layer and an opaque outer layer, the inner layer defining an interior path therethrough for accessing the surgical site, the outer layer defining an outer surface of the retractor;
   a light transmission medium disposed between the opaque inner layer and the opaque outer layer for transmitting light from a proximal end of the retractor to a distal end of the retractor, wherein the inner layer is constructed as a separate layer from the light transmission medium to protect the light transmission medium; and
   an integrated light emitter in proximity to the distal end of the one or more adjustable blades of the retractor to illuminate a surgical site accessed by the retractor.

2. The surgical retractor of claim 1 wherein the one or more adjustable blades comprise telescoping blades.

3. The surgical access system of claim 1, wherein the light transmission medium comprises fiber optic cabling.

4. The surgical access system of claim 1 wherein the light emitter is configured to transmit infrared light.

5. The surgical access system of claim 1 wherein the light emitter is configured to transmit ultraviolet light.

6. The surgical retractor of claim 1 wherein a proximal end of the retractor is configured to minimize reflection of external light.

* * * * *